United States Patent [19]

Myers

[11] Patent Number: 4,704,744
[45] Date of Patent: Nov. 10, 1987

[54] NECK AND FACE SHIELD ESPECIALLY ADAPTED TO BE WORN UNDER A HAIR DRYER

[76] Inventor: Janice L. Myers, 12523 Woods Lake Rd., Monroe, Wash. 98272

[21] Appl. No.: 885,279

[22] Filed: Jul. 14, 1986

Related U.S. Application Data

[63] Continuation-in-part of Ser. No. 769,350, Aug. 26, 1985, abandoned.

[51] Int. Cl.$^4$ ............................................. A42B 1/04
[52] U.S. Cl. ........................................... 2/174; 2/204; 2/DIG. 6; 4/515
[58] Field of Search .......... 2/174, 204, 209.3, DIG. 6; 4/515, 516, 520, 521, 514

[56] References Cited

U.S. PATENT DOCUMENTS

| | | | |
|---|---|---|---|
| 486,348 | 11/1892 | Mattson | 4/521 |
| 926,555 | 6/1909 | Ernest | 4/521 |
| 971,503 | 9/1910 | Howard . | |
| 1,283,357 | 10/1918 | Thompson | 2/174 |
| 1,593,042 | 9/1926 | Streuli . | |
| 1,741,327 | 12/1929 | Merlino | 4/521 |
| 1,750,937 | 3/1930 | Morgan | 4/521 |
| 1,764,912 | 6/1930 | Casterudell | 4/521 |
| 1,858,331 | 5/1932 | Hughes . | |
| 1,900,002 | 3/1933 | Varell | 2/174 |
| 2,136,039 | 11/1938 | Clancy | 4/521 |
| 2,226,956 | 12/1940 | Womack . | |
| 2,241,855 | 5/1941 | Heisterberg . | |
| 2,327,678 | 8/1943 | Stovall | 2/174 |
| 2,424,744 | 7/1947 | Dicken et al. . | |
| 2,447,776 | 8/1948 | Sherwood . | |
| 2,666,922 | 1/1954 | Torricelli . | |
| 2,684,072 | 7/1954 | Lewis | 4/521 |
| 2,893,403 | 7/1959 | Turman | 2/174 |
| 3,235,882 | 2/1966 | Coleman . | |
| 4,133,052 | 1/1979 | Hodgman | 2/174 |
| 4,428,079 | 1/1984 | McKee | 2/174 |
| 4,441,214 | 4/1984 | Werner et al. | 2/174 |

FOREIGN PATENT DOCUMENTS

| | | | |
|---|---|---|---|
| 19348 | of 1894 | United Kingdom | 4/521 |
| 694492 | 2/1950 | United Kingdom | 4/521 |

OTHER PUBLICATIONS

Maurice Gershman article entitled "Self-Adhering Nylon Tapes", Oct. 19, 1958, issue of the Journal of the American Medical Association, vol. 168, No. 7, p. 980.

*Primary Examiner*—Harvey C. Hornsby
*Assistant Examiner*—Mary A. Ellis
*Attorney, Agent, or Firm*—Graybeal, Jensen & Puntigam

[57] ABSTRACT

A face and neck shield to be worn under a hood type dryer, involving a wide, annularly shaped band snugly fitting the head of the wearer substantially at the hair line of the wearer and deflecting most of the air exhausted from the dryer forwardly and away from the face and neck of the wearer while nevertheless providing substantial closure of the exhaust face of the hair dryer, the wide band of the shield being held in place by adjustable interconnection means in the rear portion thereof and by over-the-head band support strap means one of which runs from front-to-rear of the band, with diverging over-the-head strap means connected to the front-to-rear strap and diverging to points of attachment at the outboard edge of the band, substantially radially outwardly of the temples of the wearer, to provide positive band support thereat, the front-to-rear strap being frontally connected to the inboard edge of the band so that the front of the band over the face of the wearer, droops slightly in visor-like fashion under action of the heated air exhausted from the air dryer, thus deflecting most of such air forwardly and away from the face and the neck of the wearer.

4 Claims, 4 Drawing Figures

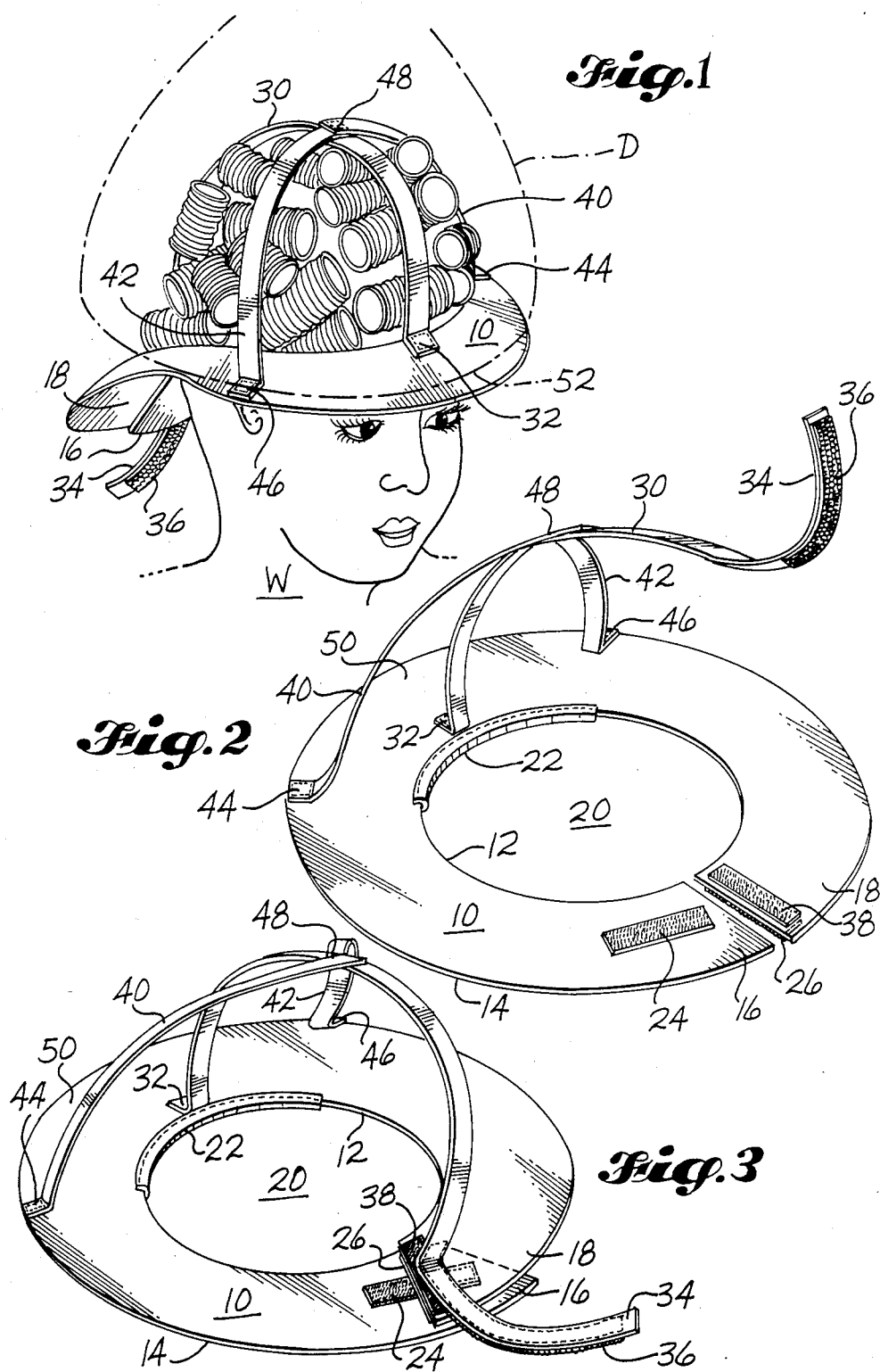

NECK AND FACE SHIELD ESPECIALLY ADAPTED TO BE WORN UNDER A HAIR DRYER

CROSS REFERENCE TO RELATED APPLICATION

This application is a continuation-in-part of my U.S. patent application Ser. No. 769,350 entitled "Neck and Face Shield", filed Aug. 26, 1985, and now abandoned.

BACKGROUND OF THE INVENTION

1. Field of the Invention

This invention relates to neck and face shields and more particularly to neck and face shields especially adapted to be worn by a person wearing hair curlers and drying one's hair while sitting under a hood type hair dryer of a type commonly used in beauty parlors.

2. Description of the Prior Art

Many efforts have been made to solve the problem incident to the exposure of the face, neck and ear portions of a person being subject to heated air blown to dry the hair of that person after washing of the hair, usually with the hair in curlers, while the person is sitting under a hair dryer of the type commonly used in beauty parlors. The need is for shielding in one form or another of the face and neck of the person, without obstruction or with only minimal obstruction of the heated air flow through the hair being dryed, it of course being preferable in designing such a shield for the shield to have the capability of fitting various sizes of heads and hair arrangements, particularly when the hair of the person whose hair is being dried is rolled on large curlers, as is common practice.

Considered the most relevant of prior hair drying shields known to me, in terms of similarity to the design of the shield of the present invention, is the shield disclosed in Stovall U.S. Pat. No. 2,327,678, which involves a circumferentially adjustable, annular shield, which is placeable around the head of the user and which is essentially frusto-conical in form, the location of the shield on the head of the user being determined by a ribbon or thread 16 led from an inboard location on the shield laterally across the top of the head of the user then around the inner portion of the shield to a rearward point inboard on the shield, then forwardly across the top of the head of the user to a juncture or joining point with the first pass of the ribbon or thread, such as shown in FIGS. 1 and 3 of the patent. As indicated, and as shown in its FIGS. 2 and 5, for example, the Stovall shield is essentially frusto-conical in nature, and there is no support of the shield in any of its outboard portions except by reason of its frusto-conical configuration. In use of such a shield, however, a frusto-conical configuration is inherently disadvantageous in that, when so worn, a compromise must be made between the amount of hair of the wearer which is left above the shield and the spacing of the outer edge of the shield from the lower edge of the hair dryer. Also, since only the inner edge of the shield is supported, by contact of such inner edge with the head of the wearer and by the cross thread or ribbon 16, the Stoval shield tends to be deflected downwardly by the blown air flow out through the gap between the outer edge of the shield and the lower edge of the dryer so that much of the heated air does not serve the intended purpose i.e., the drying of the wearer's hair.

More or less frusto-conical air drying shields are also disclosed in Thompson U.S. Pat. No. 1,283,357, Torricelli U.S. Pat. No. 2,666,922, Sherwood U.S. Pat. No. 2,447,776 and Heisterberg U.S. Pat. No. 2,241,855, and a similar shield of an essentially planar nature is disclosed in Womack U.S. Pat. No. 2,226,956. Also of interest is the head piece disclosed in Turman U.S. Pat. No. 2,893,403 which involves a curler protecting head piece having a lower adjustable band encircling the head, but without any shield extending therefrom. Of interest, also, is a letter to the editor authored by Maurice Gershman under the heading "SELF-ADHERING NYLON TAPES", which appears in the Oct. 19, 1958 issue of the Journal of the American Medical Association, Volume 168, Number 7, at page 980.

Also of interest, having been cited on this basis in the course of the prosecution of my parent patent application Ser. No. 769,350 are Thompson U.S. Pat. No. 1,283,357, Merlino U.S. Pat. No. 1,741,327, Morgan U.S. Pat. No. 1,750,937, Caster-Udell U.S. Pat. No. 1,764,912, Varell U.S. Pat. No. 1,900,002, Hodgman U.S. Pat. No. 4,133,052, and McKee U.S. Pat. No. 4,428,079.

Additional prior art patents, also of general interest, cited by me in said patent application Ser. No. 769,350 are Howard U.S. Pat. No. 971,503, Streuli U.S. Pat. No. 1,593,042, Hughes U.S. Pat. No. 1,858,331, Dicken et al U.S. Pat. No. 2,424,744 and Coleman U.S. Pat. No. 3,235,882.

SUMMARY OF THE INVENTION

The neck and face shield of the present invention provides a generally circular shaped wide band which is adjustable to snugly fit around the head of the wearer below the hair line with sufficient support of the band to provide substantial closure of the exhaust face of the associated hair dryer, to limit the escape of heated air from the dryer and in turn increase the efficiency of the hair drying action, with the primary deflection of heated air exhausting from the dryer being well forwardly of the face of the wearer of the shield. To provide this configuration of the shield in use, the annular band is supported in the outer portions thereof by over-the-head strap means engaging the band approximately radially outwardly of the temples of the wearer, i.e., at points situated at angles of about 60° from the front center point of the band.

It is a further feature and advantage of the hair and neck shield of the present invention that it is fabricated in its band portion of impermeable, double thickness nylon or like sheet having sufficient body to prevent undue drooping and sagging of the band while worn and to protect against undue exposure of the user's ears, face and neck to heated air flowing from the dryer. The configuration of the shield as worn is also such as to limit liquid drainage over the face and neck of the user during the time while the user is exposed to permanent wave solutions.

A further feature of the neck and face shield of the present invention is that it can be worn to advantage when one is applying makeup to facial features by preventing the hair of the user from falling down over the user's face during the period of applying makeup.

Yet another advantageous feature of the neck and face shield of the present invention is its full adjustability to be fit laterally and snugly around the head of any wearer and also its adjustability to ride at a appropriate level on the head of the wearer so as to essentially lie below the hair of the wearer when the user's hair is made up in curls, or otherwise.

Various other objects, advantages, and utilities of the present invention will be apparent from the following description and accompanying drawings portraying the preferred embodiment thereof.

BRIEF DESCRIPTION OF THE DRAWING

FIG. 1 is a perspective view of the preferred embodiment of my invention as worn by a user and as associated with a conventional hair dryer, such perspective view being taken from a forward and upper aspect;

FIG. 2 is a similar view showing the shield shown in FIG. 1 in its form prior to its being installed on the head of a user, such view being from an upper and rearward aspect, with the longitudinal over-the-head strap detached and with the rear portion of the head band separated;

FIG. 3 is a further perspective view of the structure shown in FIG. 2, showing the longitudinal strap and the ends of the head band attached together in a manner typical of the relationship thereof as worn.

DESCRIPTION OF THE PREFERRED EMBODIMENT

Figure 4:
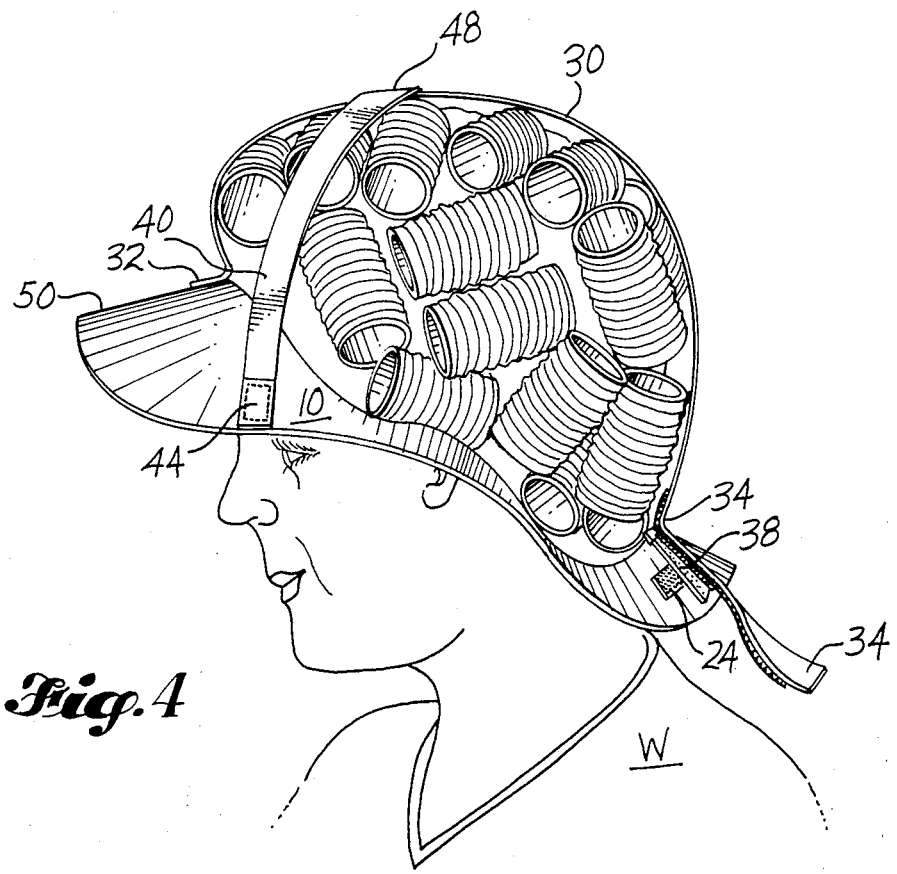
FIG. 4 is a side view of the neck and face shield of the present invention as shown in FIGS. 1-3, as installed on the head of a wearer and further showing the relationship of the head band to the hair of the wearer and also illustrating the air deflecting forward portions of the band in typical orientation under action of air exhausting from the hair dryer.

FIGS. 1 and 4 show the illustrated embodiment of the face and neck shield of the present invention as worn by a person whose hair is being dried under a hood type dryer, and FIGS. 2 and 3 show further detail of the shield, with FIG. 2 showing the shield with the rear portions open and with the front-to-rear strap thereof disengaged at the rear for placement on the head of the wearer, and with FIG. 3 showing the band end portions and the front-to-rear strap in place as the shield is worn. As will be understood, while the band portion of the shield is fabricated of flat sheet material and appears nominally flat, i.e. planar in the views of FIGS. 2 and 3, the band as worn and as shown in FIGS. 1 and 4, actually substantially follows the hair line of the wearer when worn, i.e. the inboard edge of the bank courses along the top of the forehead over the ears and then lies around the nape of the neck of the wearer substantially at the hair line, with all or substantially all of the hair of the wearer above the band, particularly when the shield is worn with the hair in curlers.

More specifically, the annular, wide band 10, typically measuring about four inches between the inboard edge 12 and the outboard edge 14 thereof, has two separable rear end portions 16,18 so that the central opening 20 defined by the inboard edge 12 may be adjusted to fit the head of a particular wearer W. A foam rubber or like segment 22 is preferably arranged in the forward portion of the inboard edge 12 of the band to render the band more comfortable as applied to the forehead of the wearer. As will be apparent, application of the shield to the wearer involves placement of the band around the head of the wearer with the inboard edge 12 of the band following the wearer's hair line, the band being snugged against the head of the wearer and the free ends 16,18 thereof interconnected at the rear of the band, Velcro strips 24,26 being suitable for the purpose and acting to firmly retain the end portions 16,18 together in overlapping relation, on an adjustable and readily detachable basis.

With the band 10 of the shield in place on the head of the wearer, the shield of the present invention is maintained in desired orientation with respect to the head and hair of the wearer by over-the-head strap means providing band positioning and band support. In the embodiments shown, the longitudinal or front-to-rear strap 30 extends from a point of attachment 32 at the front inboard edge of the band to a rear or "tail" end 34 which is adjustably attachable to the rear of the band adjacent the overlapped rear end portions 16,18, with Velcro strips 36,38 being respectively provided on band end portion 16 and on the rear end portion 34 of strap 30 for this purpose. As will be apparent, the Velcro strips 36,38 are interengaged with the band 10 in place on the head of the wearer to lie somewhat snugly over the head and hair of the wearer so that the band remains in place without tending to move lower on the head of the wearer.

The band positioning and support means further includes, in a manner characteristic of the invention, to diverging over-the-head straps 40,42, which extend from respective points of attachment 44,46 to the band substantially at the outboard edge thereof to a common point of attachment 48 to the front-to-rear strap 30, which common part of attachment 48 is about one-quarter to one-third of the way from the front end of strap 30 to the nominal point of attachment of the rear end thereof to the band. The points of attachment 44,46 of the straps 40,42 are located approximately radially outward of the temples of the wearer (noting FIGS. 1 and 4 in this respect), which arrangement provides positive band support generally at the outboard edge of the band at the sides of the forehead, the band support arrangement providing that the forward portion 50 of the band between the attachment points can droop slightly in the nature of a visor under action of the heated air exhausting from the associated hair dryer D (shown in phantom in FIG. 1), deflecting most of the air exhausting from the dryer D forwardly and away from the face and neck of the wearer W. As will be understood, the hair dryer D is conventional in form, of the hood type in common usage, the hood being downwardly open with the lower edge 52 thereof (FIG. 1) defining what may be termed an exhaust face. As will also be understood, the width of the band 10 is such that the outboard edge 14 thereof substantially spans the exhaust face 52 of the air dryer D when the shield is in place on a wearer W and the wearer is in position under the hair dryer hood to receive heated air flow.

To provide substantial closure of the exhaust face of the hair dryer by the shield as worn around the head of the wearer with deflection of most of the air exhausted from the hair dryer forwardly and away from the face and neck of the wearer, it has been found particularly advantageous to place the outboard edge supporting straps 40, 42 at points of attachment with the band adjacent its outer edge which are substantially radially outward of the temples of the wearer. Stated otherwise, the angular relation of these points of attachment 44, 46 adjacent the outboard edge 14 of the band 10 is with such points of attachment arranged substantially along radii offset from a radius to the front of the band by angles of about 60°, the front-to-rear over-the-head strap 30 being arranged along such radius to the front of the band and along a radius to the rear of the band, with attachment to the band at the inboard edge of the band at the front.

To provide sufficient body to the band of the shield it has been found desirable to fabricate such of impervious double thickness nylon or like sheet material, suitably of about 40/1000th inch thickness. So fabricated, the shield has sufficient "body" to not droop excessively even under the action of air exhausting from the hair dryer and maintain essentially its shape even when heated by such air, yet is extremely light in weight so is comfortable to wear for an extended period. It is also readily washable and sterilizeable from time to time as needed.

From the foregoing, variations and modification in the construction and form of the embodiment described will occur to those skilled in the art to which the invention is addressed, without departing from the principal features of the invention, as set forth in the following claims.

What is claimed is:

1. A face and neck shield especially adapted to be worn under a hood type hair dryer while the wearer's hair is being dried, said shield comprising:

(a) an annularly shaped, wide band having overlapping end portions rearwardly of the band, with means for detachably and adjustably securing the end portions together so that the the band snugle engages the head of the wearer substantially at the hair line of the wearer, and (b) band support means including (i) over-the-head strap means attached to the band at the front inboard edge of the band and adjustably attachable at the rear of the band, and (ii) diverging over-the-head strap means spanning the forehead of the wearer and extending down to separated points of attachment to the band substantially at the outboard edge thereof, the angular relation of the points of attachment of the over-the-head strap means, considered on the basis of radii drawn from the center of the band, being with the first strap means arranged along a radius to the front and a radius to the rear of the band, and with the points of attachment of the diverging strap means to the band being arranged substantially along radii offset from the radius to the front of the band by angles of about 60°, and the band support arrangement providing that the forward portion of the band between the diverging strap means connections thereto droops slightly under action of the heated air exhausting from the hair dryer deflecting most of the air exhausting from the dryer forwardly and away from the face and neck of the wearer.

2. A face and neck shield especially adapted to be worn under a hood type hair dryer and which is adjustable to snugly fit around the head of the wearer substantially at the hair line of the wearer and provide substantial closure of the exhaust face of the hair dryer, said shield comprising:

(a) an annularly shaped wide band having overlapping end portions rearwardly of the band, with means for detachably and adjustably securing the end portions together so that the inboard edge of the band snugly engages around the head of the wearer, the width of said band being such that the outboard edge of the band substantially spans the exhaust face of the hair dryer, and (b) band support means including (i) front-to-rear over-the-head strap means attached to the band at the front inboard edge of the band and adjustably attachable to the rear of the band adjacent the overlapped rear end portions thereof, and (ii) diverging over-the-head strap means fastened to the front-to-rear strap means about one-quarter to one-third of the way from the front end thereof and extending down to points of attachment to the band substantially at the outboard edge thereof, said points of attachment of the diverging strap means being located approximately radially outwardly of the temples of the wearer, the angular relation of the points of attachment of the over-the-head straps means, considered on the basis of radii drawn from the center of the band, being with the first strap means arranged along a radius to the front and a radius to the rear of the band, and with the points of attachment of the diverging strap means to the band being arranged substantially along radii offset from the radius to the front of the band by angles of about 60°, and the band support arrangement providing the forward portion of the band between the diverging strap means connections to thereto droops slightly under action of the heat air exhausting from the hair dryer deflecting most of the air exhausting from the dryer forwardly any away from the face and neck of the wearer.

3. A face and neck shield according to claim 2, wherein said band and said strap means are fabricated of double thickness vinyl sheet.

4. A face and neck shield according to claim 2, wherein the thickness of the band of the shield is about 40/100th inch and the inboard-to-outboard width thereof is about 4 inches.

* * * * *